US008569028B2

(12) United States Patent
Jin et al.

(10) Patent No.: US 8,569,028 B2
(45) Date of Patent: Oct. 29, 2013

(54) METHOD FOR ENCAPSULATION OF MICROPARTICLES

(75) Inventors: Xixuan Jin, Greenville, MS (US); Daniel B. Custis, Van Wert, OH (US)

(73) Assignee: The United States of America, as represented by the Secretary of the Agriculture, Washington, DC (US)

( * ) Notice: Subject to any disclaimer, the term of this patent is extended or adjusted under 35 U.S.C. 154(b) by 442 days.

(21) Appl. No.: 12/797,087

(22) Filed: Jun. 9, 2010

(65) Prior Publication Data

US 2011/0306116 A1    Dec. 15, 2011

(51) Int. Cl.
*C12N 1/04* (2006.01)
*C12N 1/12* (2006.01)
*C12N 1/20* (2006.01)
*C12N 11/00* (2006.01)
*C12N 11/10* (2006.01)
*C12N 11/16* (2006.01)

(52) U.S. Cl.
USPC ......... 435/178; 435/174; 435/252.1; 435/260

(58) Field of Classification Search
None
See application file for complete search history.

(56) References Cited

U.S. PATENT DOCUMENTS

| | | | | |
|---|---|---|---|---|
| 4,948,586 | A | 8/1990 | Bohm et al. | |
| 5,288,634 | A | 2/1994 | Harman et al. | |
| 5,750,467 | A * | 5/1998 | Shasha et al. | 504/206 |
| 5,989,898 | A | 11/1999 | Jin et al. | |
| 6,455,036 | B1 | 9/2002 | Quimby, Jr. et al. | |
| 2007/0098740 | A1 | 5/2007 | Grainger | |

FOREIGN PATENT DOCUMENTS

| | | |
|---|---|---|
| WO | PCT/US2006/034744 | 7/2006 |
| WO | WO2007030557 | 3/2007 |

* cited by examiner

*Primary Examiner* — Debbie K Ware
(74) *Attorney, Agent, or Firm* — John D. Fado; G. Byron Stover; Gail E. Poulos

(57) ABSTRACT

A method for encapsulation of microparticles (e.g., fungal conidia), involving (i) suspending microparticles in an aqueous solution containing at least one sugar to form an aqueous suspension wherein the concentration of said sugar is about 0.1 to 10% w/v, and (ii) spray drying said aqueous suspension with a spray dryer, wherein the inlet temperature of said spray dryer is about 40° C. to about 140° C. and the outlet temperature of said spray dryer is about 20° C. to about 80° C.

9 Claims, 6 Drawing Sheets

METHOD FOR ENCAPSULATION OF MICROPARTICLES

BACKGROUND OF THE INVENTION

The present invention relates to a method for encapsulation of microparticles (e.g., fungal conidia), involving (i) suspending microparticles in an aqueous solution containing at least one sugar to form an aqueous suspension wherein the concentration of said sugar is about 0.1% to about 10% w/v, and (ii) spray drying said aqueous suspension with a spray dryer, wherein the inlet temperature of said spray dryer is about 40° C. to about 140° C. and the outlet temperature of said spray dryer is about 20° C. to about 80° C.

*Trichoderma* spp. are able to control root and foliar pathogens of plants through mycoparasitism, nutrient competition and rhizosphere competence, enzymes, induced defense responses in plants, and metabolism of germination stimulants (Howell, C. R., Plant Disease, 87: 4-10 (2003)). Recent studies by Advanced Biological Marketing, Inc. (ABM) in Van Wert, Ohio and Cornell University showed that *Trichoderma* strains may induce changes in the micro floral composition on roots, enhance nutrient uptake, stabilize soil nutrients, promote root development, and increase root hair formation (Harman, G. E., Phytopathology, 96: 190-194 (2006)). *Trichoderma* spp. produces three kinds of propagules (or structures that can give rise to a new individual organism): hyphae, chlamydospores, and conidia (Papavizas, G. C., Annual Review of Phytopathology, 23: 23-54 (1985)). Biomass that contains hyphae as the main propagules of *Trichoderma* spp. cannot withstand drying and loses viability during dehydration. Conidia can be produced abundantly in a short period of time, and therefore have been used as the active ingredient in most *Trichoderma* spp. based products. Efforts have been made to produce chlamydospores and desiccation tolerant conidia from liquid fermentation (Harman, G. E., et al., Biological Control, 1:23-28 (1991); Jin, X., et al., Biological Control, 1: 237-243 (1991); Jin, X., et al., Biological Control, 7: 267-274 (1996); Eyal, J., et al., Journal of Industrial Microbiology & Biotechnology, 19:163-168 (1997)). Companies engaged in the development of *Trichoderma* conidia based products are usually small and lack the financial support to build up large liquid fermentation facilities. *Trichoderma* conidia are currently produced by two-phase solid fermentation systems. Inoculum is produced by liquid culturing and then transferred to a solid matrix for aerial conidial production by solid fermentation. Aerial conidia of *T. harzianum* are hydrophilic in nature and it is difficult to separate them from the solid substrate by sieving. Washing conidia off the solid fermentation substrate and then centrifuging the suspension has become the choice for harvesting. Conidia produced by either liquid fermentation or two-phase solid fermentation must be dried to prevent spoilage by microbial contamination and to induce dormancy for formulation development and shelf-life (Jin, X., et al., Principles in the development of biological control systems employing *Trichoderma* species against soil-born plant pathogenic fungi, In: Leatham, G. F. (Ed.), "Frontiers in industrial mycology", 1992, Chapman & Hall, Inc., New York, N.Y., pp. 174-195). Drying the conidial pastes of *Trichoderma* spp. in large scale production remains a major hurdle because conidia lose viability during the drying process at elevated temperatures.

There are three drying technologies employed most often by industry: fluid bed-, freeze-, and spray-drying. Freeze drying has been used to preserve microorganisms for decades and is the preferred method for keeping culture collections worldwide (Morgan, C. A., et al., Journal of Microbiological Methods, 66: 183-193 (2006)). The disadvantages of freeze-drying are cross contamination, viability loss, and high costs of processing. Furthermore, our experience showed that it was difficult to break freeze dried cakes of *Trichoderma* conidia, and the conidia lost viability because of the heat generated by milling. Fluid bed drying is usually used to process relatively large particles for glomeration and particle coating. A contact-sorption drying method was developed to dry *Penicillium bilaii* in a fluidized bed dryer (Tadayyon, A., and G. A. Hill, Journal of Chemical Technology and Biotechnology, 68: 277-282 (1997)). Fungal spores in a liquid suspension were injected into the dryer using an air-shear atomizer from the top of the dryer. Instant skim milk powder was fluidized as a protecting agent, moisture sorbent, and carrier. The resulting product survived well in refrigeration for 3 months, but only survived several days under room temperatures. Spray-drying is mostly used in the dairy industry because of the relatively low cost compared to freeze-drying (Morgan et al., 2006). Spray-drying was used to process several fungal conidia, including conidia of *Trichoderma harzianum*, without success (Larena, I., et al., Journal of Applied Microbiology, 94: 508-514 (2003); Guijarro, B., et al., Biocontrol Science and Technology, 16: 257-269 (2006); personal communication with Dan Custis and Gary Harman, 2009). Comparison of drying methods were conducted to study the effects of freeze-, spray-, and fluid bed-drying on conidia viability of *Epicoccum nigrum* and *Penicillium frequentans*, biological control agents against *Monilinia* spp. that cause peach brown rot disease, and *P. oxalium* for the control of *Fusarium* wilt of tomatoes (Larena, I., et al., Journal of Applied Microbiology, 94: 508-514 (2003); Larena, I., et al., Journal of Phytopathology, 151: 600-606 (2003); Guijarro, B., et al., Biocontrol Science and Technology, 16: 257-269 (2006)). Spray drying resulted in considerable loss of conidial viability. Comparison of drying technologies was also conducted in drying conidia of entomopathogenic fungi *Beauveria brongniartii* and *Metarhizium anisopliae* (Horaczek, A., and H. Viernstein, Biological Control, 31: 65-71 (2004)). Spray drying caused severe damage to the conidia and resulted in low viability and prolonged germination.

Microencapsulation can enhance the activity of some biological control agents and protect them from adverse conditions in preparing bioherbicide inocula (Winder, R. S., et al., Biocontrol Science and Technology, 13:155-169 (2003)). Attempts have been made in microencapsulation of nuclear polyhedrosis virus, *Bacillus thurigenisis*, and hydrophobic aerial conidia of *Metarhizium anisopliae* and *Beauveria bassiana*, which are used in biological control of insects (U.S. Pat. No. 4,948,586; Horaczek and Viernstein, 2004; Liu, C. P., and S. D. Liu, Journal of Microencapsulation, 26: 377-384 (2009); Liu, C. P., and S. D. Liu, Drying Technology, 27: 747-753 (2009)). An encapsulation method was also developed for either ascospores or conidia of potential biological control agents, including *Talaromyces flavus, Gliocladium virens, Pennicillum oxalicum*, and *Trichoderma viride* (Fravel, D. R., et al., Phytopathology, 75: 774-777 (1985)). Conidia were encapsulated in an alginate-clay matrix and were dried at room temperature. New systems of encapsulating *Trichoderma* spp. have been developed and applied to several *Trichoderma* species and strains (Cho, C. F., and W. C. Lee, Journal of Bioscience and Bioengineering, 87: 822-824 (1999); Mafia, R. G., et al., Fitopatologia brasileira, 28: 101-105 (2003); El-Katatny, M. H., et al., Food Technology and Biotechnology, 41: 219-225 (2003)). *Trichoderma* mycelium and conidia were encapsulated in pellets containing gluten, wheat bran, rice husk, oak bran, maize meal, or chitin as nutrient base. However, the density of conidia in the alginate pellets is low, and the shelf life is not enough to support commercialization of *Trichoderma* based products. Furthermore, alginate encapsulation is difficult to scale up because it is labor intensive, and air drying pellets at room temperatures takes a long time, requires a large space, and easily gets contaminated. An encapsulation technology was developed using water insoluble absorbents to remove the water gently from the conidial biomass at room temperature and to encapsulate the conidia (U.S. Patent Application Publication No. PCT/US2006/034744 (2006)). The water insoluble, water-absorbent substances can be any organic or inorganic material capable of removing moisture gently from the suspension of *Trichoderma* conidia. The disadvantage is that the final product contains 80-90% of water insoluble, water-absorbent substances which result in blocked pipelines in field applications (Custis, 2007, personal communication). It is ideal that *Trichoderma* formulations should contain $5 \times 10^9$ cfu/g to be effective in a variety of applications (U.S. Patent Application Publication No. PCT/US2006/034744 (2006)). Conidial density or quantity in the dried formulation of *Trichoderma* is critical for field application because higher conidial density in a formulation should result in better efficacy. To achieve this conidial density in any formulation, efforts must be made to provide technical powders that contain at least 90% of pure conidia.

We have developed a method for the microencapsulation of conidia (e.g., *T. harzianum*) through spray-drying which significantly improved the survival percentages of conidia and resulted in a high concentration of viable conidia in the final product after drying.

SUMMARY OF THE INVENTION

In accordance with the present invention there is provided a method for encapsulation of microparticles, involving (i) suspending microparticles in an aqueous solution containing at least one sugar to form an aqueous suspension wherein the concentration of said sugar is about 0.1% to about 10% w/v, and (ii) spray drying said aqueous suspension with a spray dryer, wherein the inlet temperature of said spray dryer is about 40° C. to about 140° C. and the outlet temperature of said spray dryer is about 20° C. to about 80° C.

DETAILED DESCRIPTION OF THE INVENTION

The present invention relates to a method for encapsulation of microparticles (e.g., fungal conidia), involving (i) suspending microparticles in an aqueous solution containing at least one sugar to form an aqueous suspension wherein the concentration of said sugar is about 0.1% to about 10.0% w/v (e.g., 0.1%-10.0% w/v), and (ii) spray drying said aqueous suspension with a spray dryer, wherein the inlet temperature of said spray dryer is about 40° C. to about 140° C. (e.g., 40° C. to 140° C.; preferably about 50° C. to about 80° C. (e.g., 50° C. to 80° C.)) and the outlet temperature of said spray dryer is about 20° C. to about 80° C. (e.g., 20° C. to 80° C.; preferably about 25° C. to about 45° C. (e.g., 25° C. to 45° C.)).

The method is applicable to a variety of microparticles and viable cellular biomaterial, including yeast cells, somatic cells and sexual cells. Of particular interest is the encapsulation of viable fungal propagules (e.g., conidia, spores, hyphal cells; preferably conidia), useful as biocontrol agents, and synthetic spores. Encapsulation of microparticles includes living cells, propagules of living cells, bacteria (e.g., *Bacillus* species such as *B. thuringiensis*)), protozoa, nematodes (e.g., *Steinernema* species, *Heterorhabditis* species), viruses, fungi and the like. Microparticles also include propagules of eukaryotic biocontrol agents microparticles (e.g., propagules of eukaryotic biocontrol agents). Fungi that can be encapsulated include *Metarhizium* species. (e.g., *M. anisopliae*), *Beauveria* species (e.g., *B. bassiana*), *Penicillium* species, *Entomophaga* species (e.g., *E. maimaiga*), *Paecilomyces* species (e.g., *P. fumosoroseus*), and *Trichoderma* species (e.g., *T. harzianum*); also microbes that improve plant nutrient uptake and yields, such as *Bradyrhizobium* species and *Rhizobium* species. The cellular biomaterial may be produced in any types of cultures, including liquid fermentation and solid fermentation. The sugar is generally monosaccharides, such as glucose (dextrose), fructose, galactose, xylose and ribose; disaccharides, such as sucrose, lactose, maltose, trehalose and cellobiose; polysaccharides, such as starch and derivatives, cellulose and derivatives; natural gums; sucrose, molasses; glycerol; honey; corn-syrup and maple syrup, or mixtures thereof. The amount of said sugar loaded on the encapsulated microparticle is about 2 to about 10 mg per one gram, of encapsulated microparticles.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and Methods: *T. harzianum* strain was provided by ABM. Frozen vials containing conidia of *T. harzianum* in 15% glycerol solution were thawed under room temperature. An inoculum transfer loop was used to transfer the *T. harzianum*-glycerol suspension to potato dextrose agar (PDA) plates. Incubation was conducted at 28° C. for 7 days until densely sporulated colonies covered the plates. Discs (1 cm in diameter) were cut half-way between a growing colony center and the colony edge in a culture plate, and were transferred to fresh made PDA plates for further enhancement of growth vigor under the same growth conditions.

Conidial production by two-phase solid fermentation: The liquid phase was used for the production of inoculum in shake cultures. Each liter of liquid medium contained 10 g potassium nitrate, 5 g potassium dihydrogen phosphate, 1.3 g anhydrous magnesium sulfate, 0.02 g ferric chloride, 8 g sucrose, 90 ml glycerol, 0.1 ml Antifoam 204 (Sigma-Aldrich, St. Louis, Mo.), and 1 ml of trace element solution (made by dissolving the following elements to 100 ml of deionized (DI) water: 0.35 g zinc sulfate, 0.04 g cupric sulfate, 0.031 g manganese sulfate, and 0.013 g ammonium molybdate). Autoclave was conducted at 121° C. for 15 minutes and allowed to cool prior to use. Four discs were cut from approximately equal distance to the edge and to the center of a *T. harzianum* culture covered plate, and transferred to a 1 L Erlenmeyer flask containing 700 ml of the liquid medium. The flasks were placed on a Gyromax™ 747R rotary shaker (Amerex Instruments, Inc., Lafayette, Calif.) and shaken at 150 rpm at 30° C. for four days. The culture flask was then placed on a stir plate with stirring to maintain a uniform suspension.

The solid phase was for the production of aerial conidia of *T. harzianum*: Five hundred grams of rice chaff (Producers Mill, Greenville, Miss.) was mixed with 500 g of extra long grain enriched rice (Riceland Foods, Inc., Stuttgart, Ak.) in a SACO₂ Microsac-(SACO₂, Nevele, Belgium) bag. 1200 ml of DI water was added to the mixture in the bag. The bags were sealed using a heat bag sealer (Impulse Sealer, Type AIE-500, American International Electric 2835 Pellissier Place, Whittier, Calif.). Sealed bags were placed on the bench and allowed to soak for 24 hours. Autoclave was conducted at 121° C. for 70 minutes. The autoclaved bags were cooled down at ambient temperature for 24 hours. Each bag was cut open aseptically, and the solid medium was poured into a plastic box (57.9×42.4×17.8 cm³, Rubbermaid Snaptoppers, Fairlawn, Ohio) which had been disinfected using a 10% disinfectant bleach solution (5.25% sodium hypochloride solution) followed by 70% alcohol. One hundred fifty ml of inoculum from the shake flask culture (described above) was injected into each box using a sterile syringe, and mixed with a spatula under a Bio-Safety Hood. After the tops were placed on the boxes, the boxes were sealed with tape. Boxes were then incubated in a growth room at 28° C. for 10 days.

At harvesting, 7 L of sterile deionized (DI) water was added to each box under a Bio-Safety Hood. The mixture suspension in the box was stirred to wash conidia from the solid medium. The resulting suspension was poured through a 100 mesh screen and collected into sterile 10 L bottles. The conidia suspension was centrifuged in a Thermo Sorvall Evolution RC Superspeed Centrifuge with a TZ-28/GK Continuous Flow Centrifugation System (Kendro Laboratory Products, Newtown, Conn.) at 10,000 rpm. After centrifugation, conidial pastes were collected for microencapsulation.

Conidial production by liquid fermentation: Inoculum used to start the liquid fermentation runs was prepared as described in "Conidial production by two-phase solid fermentation" above. Liquid fermentation was conducted in a 15-L Biostat® C fermenter (Sartorius BBI Systems Inc., Bethlehem, Pa.) with a working volume of 10 liters. The fermentation process was controlled by software, MFCS/WIN Operation system, Version 2.1 (B. Braun Biotech Inc. USA, now Sartorius BBI Systems Inc.) installed on a Dell computer with Window XP Operation System. Growth medium for fermentation runs was the same as the one used for liquid inoculum production. Nine liters of growth medium was added to the fermentation vessel. Inline sterilization was then performed at 121° C. for 30 minutes. Sterile DI water was added to the fermentation vessel when the medium was cooled down to 28° C. to bring the volume back to 9 liters. One liter of inoculum from a 4-days shake flask culture of *T. harzianum* was added to the fermenter. The fermentation temperature was 28° C. The pH of fermentation medium was not controlled during the process. Dissolved oxygen was calibrated to 0 by removal of oxygen through sterilization and to 100% by air saturation. During fermentation, dissolved oxygen was controlled at 50% saturation of air, and stir speed was maintained at 100 rpm. Fermentation run was 72 hours in duration, and then the entire fermentation broth was harvested from the bottom harvesting valve. Each 2 liters of fermentation broth was homogenized using a Waring Laboratories Heavy Duty Laboratory Blender (Waring Commercial, New Hartford, Conn.) at high speed for 30 seconds. Homogenized fermentation broth was divided into 50 ml Falcon centrifuge tubes and centrifuged at 4000 rpm for 6 minutes in an Eppendorf 5810 R centrifuge. The resulting paste was then stored at 4° C. until use.

Microencapsulation. Spray dryer: Microencapsulation was accomplished through spray drying. A BÜCHI Mini Spray Dryer B-290 (BÜCHI Labortechnik AG, Flawil, Switzerland) was employed to complete microencapsulation and drying. UZero Grade compressed air was supplied by Airgas Inc. (Radnor, Pa.). Aspiration was set at 100% that should translate into approximately 38 m³ per hour. Pump speed was approximately 3 ml per minute, and Nozzle Clean was set at 5. Air Flow at this unit was set at 30 mm. Cold water from a ice bath was pumped at approximate 65-70 ml per minute through the spray nozzle assembly using a Bio-Rad Variable Speed Pump (Hercules, Calif.). A sample container was placed on a stir plate with stirring to maintain the suspension. The Spray Dryer was allowed to equilibrate at the set temperature. Following equilibration, sterile DI water was aspirated through the spray nozzle for 5 minutes. The sample aspiration was started immediately following the aspiration of sterile DI water. After the spray drying of the sample was completed, the microencapsulated conidia were removed from the collection vessel and stored at 4° C. until use. Sterile DI water was pumped into the spray dryer again to clean the system for 2-3 minutes.

Determining the optimal concentration of selected sugar for microencapsulation: Different sucrose concentrations were used in this study to determine the optimal sucrose concentration for microencapsulation. Samples of 50 g of conidial paste from two-phase solid fermentation were resuspended in 100 ml of 0.5%, 1%, 2%, 4%, 6% and 8% of sucrose solutions in sterile DI water (w/v), respectively. Spray drying and microencapsulation were conducted at 60° C. A sample of 0.05 gram of spray dried conidia was resuspended in 10 ml of sterile DI water, and then vortexed for one minute for the determination of conidial counts and cfu/g. Conidial numbers were directly counted using a Hemacytometer (Hausser Scientific, Horsham, Pa.) under a light microscope. The cfu numbers were determined by plating the appropriate serial dilutions of conidial suspension on PDA plates amended with Igepal® Co-630 (Applied Science Labs, Deerfield, Ill.) to limit colony diameter (Norton, J. M. and Harman, G. E., Canadian Journal of Botany, 63: 1040-1045 (1985)). Streptomycin sulfate and chlortetracycline hydrochloride, each 0.1 g, were also added to one liter of PDA medium to eliminate bacterial contamination. The survival percentage, as a parameter of desiccation tolerance of conidia in the dried preparations, was calculated as the ratio of cfu/g divided by conidia/g (Jin et al., 1991).

Survival percentages of microencapsulated conidia from different sugar concentrations were compared and the lowest sugar concentration that resulted in highest survival percentage was the optimal sucrose concentration for microencapsulation.

To test the actual amount of sugar microencapsulated on the conidia, distilled water was used to dissolve the sugar on the conidia. Two grams of conidia either microencapsulated with optimal sugar concentration or the highest sugar concentration were re-suspended in 100 ml of distilled water, stirred for 30 minutes, and then centrifuged in an Ependorf 5810 R at 4000 rpm for 5 minutes. 10 ml of the supernatant was pipetted into a sample pan and place on a Mettler Toledo 1-1843 Halogen Moisture Balance (Mettler-Toledo, Inc., Columbus, Ohio) to determine the dry matter. Calculation was then conducted to find the actual amount of sucrose microencapsulated on the conidia.

Determining the optimal spray drying temperature for microencapsulation: Fifty grams of conidial paste from two-phase solid fermentation was mixed with 100 ml of the selected sucrose solution as described previously. Inlet temperatures for spray drying included in this study were 40°, 60°, 80°, 100°, 120°, and 140° C. Outlet temperature was recorded at 10 minute intervals to calculate the average outlet temperature at each inlet temperature settings. Survival percentages of microencapsulated conidia from each temperature level were compared and the temperature that resulted in the highest survival percentage was the optimal spray drying temperature for microencapsulation. Water activities of the encapsulated conidia were determined by a AquaLab Model Series 3 TE (Decagon Devices, Inc., Pullman, Wash.).

Microencapsulation of *T. harzianum* conidia with other sugars: This study was designed to investigate microencapsulting *T. harzianum* conidia with two other sugars, molasses and glycerol. Conidia used in this study were produced by two-phase solid fermentation. After centrifuge, 30 g of conidial paste was mixed with 40 ml of 2% sugar solution (either molasses or glycerol). Thirty grams of conidial paste was mixed with 40 ml sterile DI water as control. The re-suspended mixtures were then centrifuged again in an Ependorf 5810 R (Eppendorf AG, Hamburg, Germany) at 4000 rpm for 6 minutes. Conidial pastes from each centrifuge tubes were collected, spread in pans, and then air dried under a Bio-Safety Hood at room temperature to a moisture level around 6%. Dry preparations were used to examine the total conidial numbers and colony forming units (cfu). Samples of 0.05 g were taken from each dried preparation and transferred to a test tube containing 10 ml of sterile DI water. After 1 hour of soaking, each suspension was hothogenized at high speed using an OMNI GLH homogenizer (OMNI International, Kennesaw, Ga.) for 30 seconds to get a uniform conidial suspension.

Microencapsulation of conidial biomass produced from liquid fermentation: Fifty grams of conidial paste harvested from liquid fermentation runs was mixed with 100 ml of the selected sucrose solution as described previously, and then microencapsulated through spray drying. Inlet temperatures for spray drying included in this study were 60° C. Total conidia counts/g, cfu/g and survival percent after drying were recorded. Only one fermentation run was conducted, and therefore no statistical analysis was performed.

Scanning electron microscopic studies: Microencapsulated conidia were affixed to aluminum stubs with carbon tape, coated with gold/palladium using a Polaron E5100 sputter coater (Quorum Technologies, Newhaven, UK), and viewed on a JEOL JSM-6500F scanning electron microscope at 5 kv (JEOL USA, Peabody, Mass.). Photos were taken with conidia microencapsulated with 0%, 2%, and 8% of sucrose. Particle size of microencapsulated conidia was measured under the electron microscope and expressed as μm.

Statistical Analysis: All experiment designs were randomized complete blocks and repeated three times (except Microencapsulation of conidial biomass produced from liquid fermentation that was run only once). Conidia/g and cfu/g were log-transformed, and standard errors were calculated. Conidial biomasses used in these studies were produced from different batches; the comparisons among log conidia/g and log cfu/g were not relevant, so only survival percentages were subjected to ANOVA, Mixed Model analysis and the Least Square Post Hoc tests (Linen et al., SAS for Mixed Model, Second Ed., SAS Institute Inc., Cary, N. C. (2006).

Figure 1:
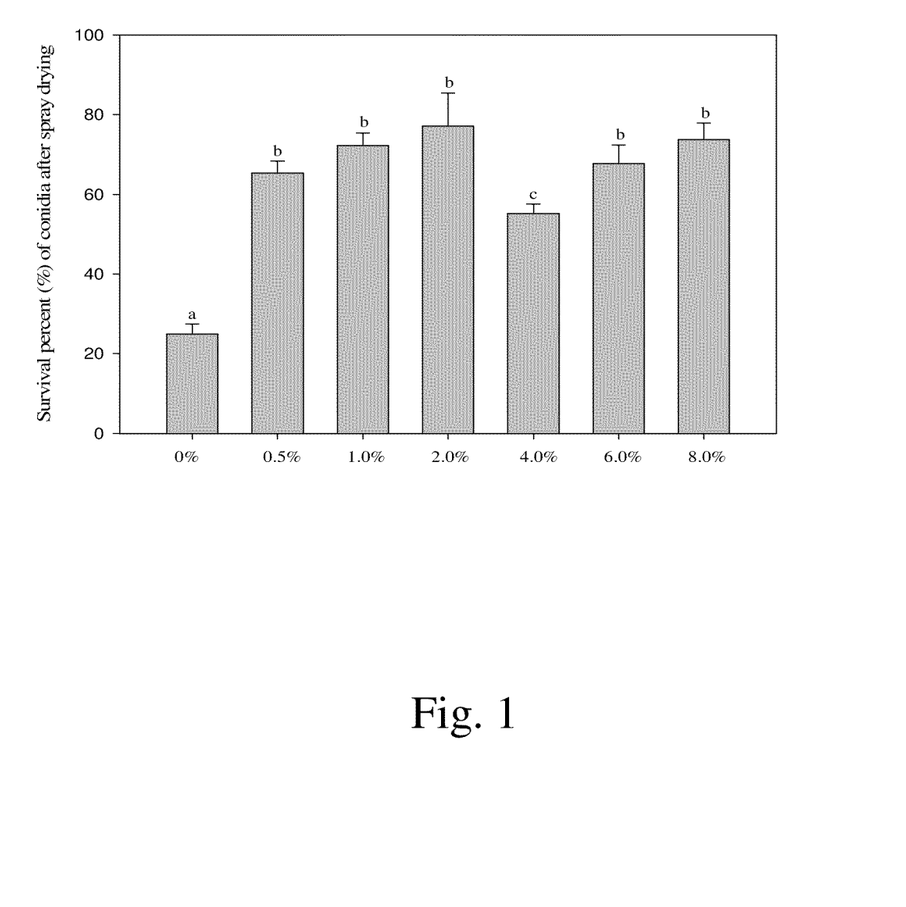
FIG. 1 shows survival percentages of *T. harzianum* conidia microencapsulated with different concentrations of sucrose solutions and spray dried in a BÜCHI Mini Spray Dryer B-290 at an inlet/outlet temperature of 60°/31° C. as described below. Each value is the mean of three replicates; verticle bars represent standard errors. Means with different letters are significantly different (P<0.05).

Results. Optimal concentration of selected sugar for microencapsulation: After drying, the cfu/g numbers in sucrose microencapsulated conidia biomasses were surprisingly higher than the cfu/g without sucrose microencapsulation regardless of the conidial counts in the biomasses (Table 1). Microencapsulation of conidia with sucrose through spray drying surprisingly and significantly (F=23.90, P<0.05, df=54) improved the survival percentages of viable conidia in the dried biomasses regardless of sucrose concentrations (FIG. 1). The best survival percent surprisingly was obtained using 2% sucrose solution. The actual amount of sucrose loaded on each gram of conidia was 3.4 mg when 2% sucrose solution was employed in microencapsulation process by spray drying, while 7.6 mg sucrose was loaded on each gram of conidia when 8% sucrose solution was used.

Figure 2:
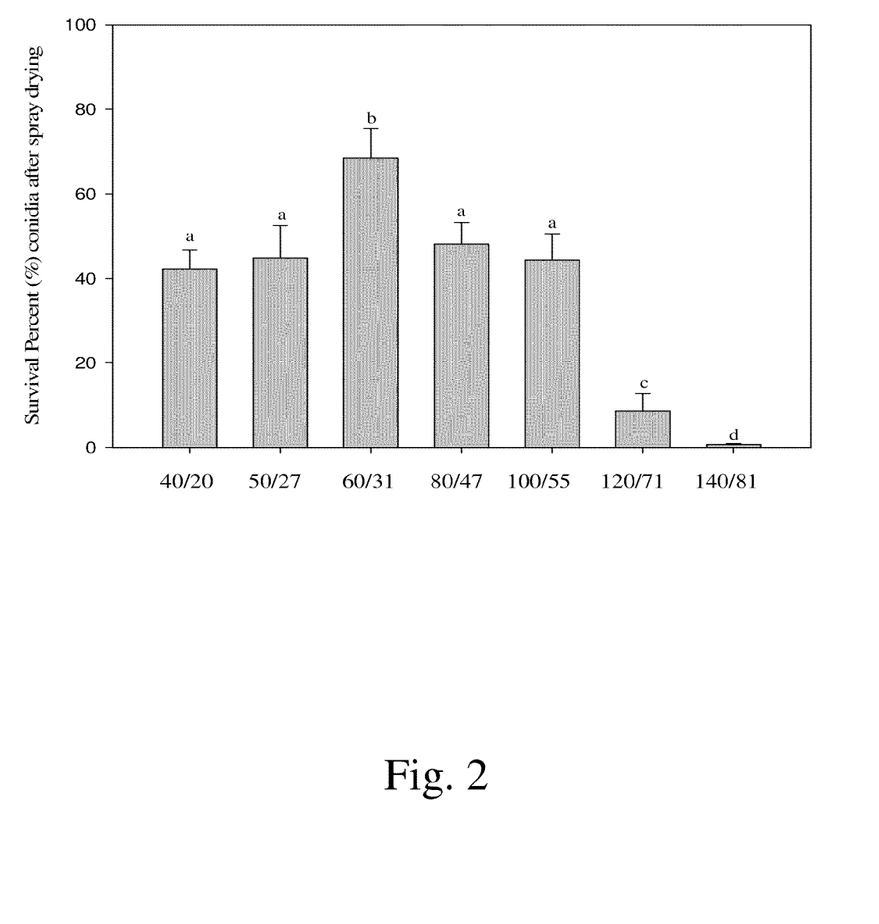
FIG. 2 shows survival percentages of *T. harzianum* conidia microencapsulated with 2% sucrose solutions (w/v) and spray dried in a BÜCHI Mini Spray Dryer B-290 at different inlet/outlet temperature (° C.) levels as described below. Each value is the mean of three replicates; verticle bars represent standard errors. Means with different letters are significantly different (P<0.05).

Optimal spray drying temperature for microencapsulation: Inlet temperatures of 40°, 50°, 60°, 80°, 100°, 120°, and 140° C. resulted in outlet temperatures of 20°, 27°, 31°, 47°, 55°, 71°, and 81° C., respectively. Although conidial biomasses were from different production batches, 2% sucrose microencapsulation by spray drying at inlet/outlet temperature settings from 50° to 80°/27° to 47° C. surprisingly yielded the highest cfu/g numbers when compared with other inlet temperature levels (Table 2). 2% sucrose solution encapsulated conidial biomass dried at a 60°/31° C. inlet/outlet temperature setting resulted in surprisingly and significantly (F=17.96, P<0.05, df=12) higher survival percentage (FIG. 2) than the survival percentages of all other inlet drying temperature levels. It was observed that when inlet/outlet temperature was at 40°/20° C. water condensation appeared on the wall of the drying cylinder, which indicated that the drying process was not well controlled. Higher inlet/outlet temperature settings, 120° C. to 140° C./71° C. to 81° C. surprisingly yielded significantly lower cfu/g (P<0.05).

Figure 3:
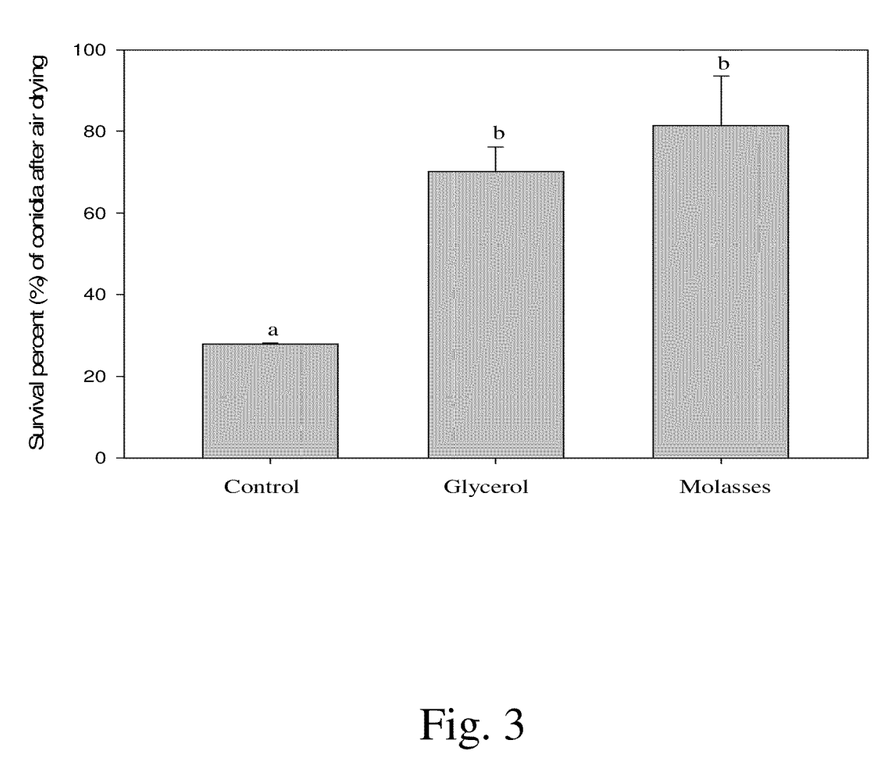
FIG. 3 shows survival percentages of *T. harzianum* conidia microencapsulated with 2% solutions (w/v) of either glycerol or molasses, and dried at ambient room temperature as described below. Each value is the mean of three replicates; verticle bars represent standard errors. Means with different letters are significantly different (P<0.05).

Microencapsulation of *T. harzianum* conidia with other sugars: Microencapsulation of conidia with either molasses or glycerol resulted in surprisingly higher cfu/g than the non-microencapsulated control regardless of conidial counts in the biomass (Table 3). Conidia microencapsulated with either molasses or glycerol had surprisingly and significantly (F=10.92, P<0.05, df=4) higher survival percentages (FIG. 3) when compared to the non-treated control. There was no significant difference (P>0.05) between these two sugar encapsulation treatments in survival percentages, although molasses microencapsulation surprisingly resulted in the highest cfu/g and survival percentage after drying.

Microencapsulation of conidial biomass produced from liquid fermentation: After spray drying, the total conidial numbers in 2% sucrose microencapsulated and non-microencapsulated conidial biomasses were $2.8 \times 10^{10}$ and $3.3 \times 10^{10}$, respectively. However, the cfu/g of microencapsulated conidial biomass was $9.3 \times 10^9$, which surprisingly represented a 33.21% survival percentage, while the cfu/g without microencapsulation was only $4.8 \times 10^9$ representing a survival percentage of 14.55%.

Figure 4:
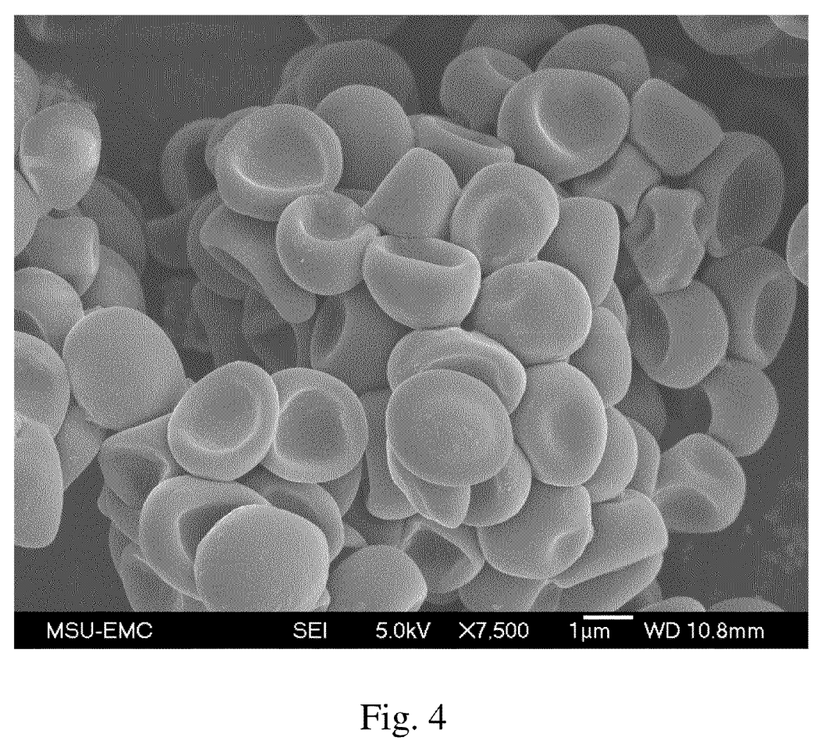
FIG. 4 shows scanning electron microscopic photo of spray dried conidia without sugar microencapsulation at an inlet/outlet temperature of 60°/31° C. using a BÜCHI Mini Spray Dryer B-290, as described below; conidia were raisin shaped and had smooth surfaces.
Figure 5:
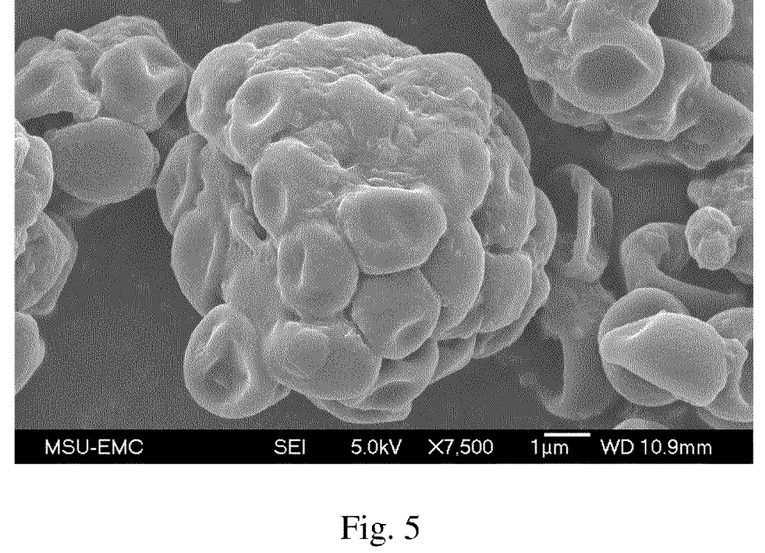
FIG. 5 shows scanning electron microscopic photo of spray dried conidia microencapsulated with 2% sucrose solution (w/v) at an inlet/outlet temperature of 60°/31° C. using a BÜCHI Mini Spray Dryer B-290 as described below.
Figure 6:
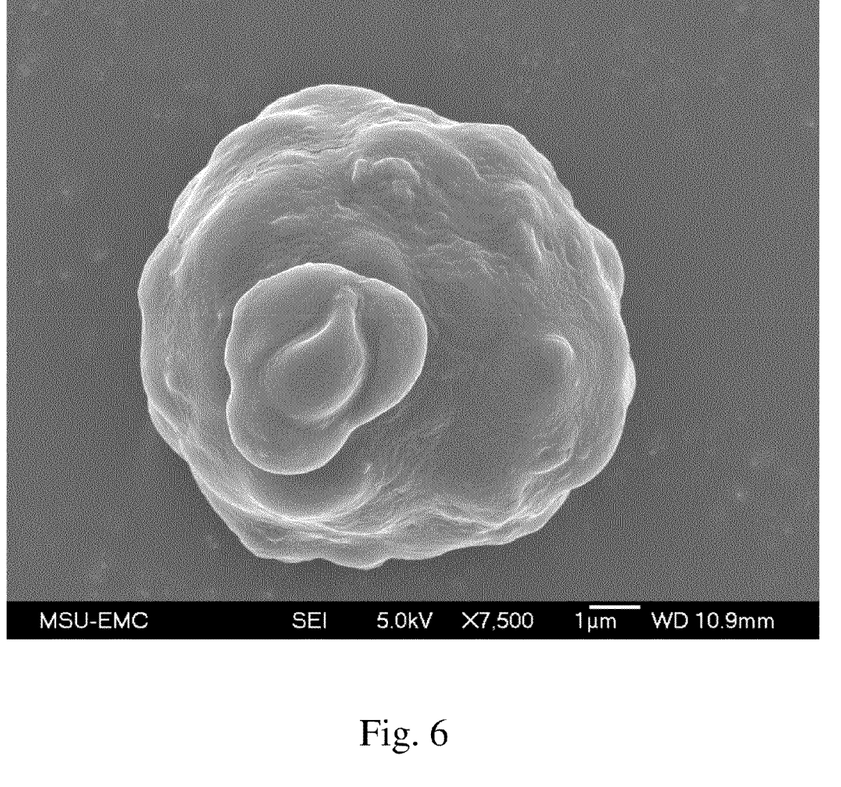
FIG. 6 shows scanning electron microscopic photo of spray dried conidia microencapsulated with 8% sucrose solution (w/v) at an inlet/outlet temperature of 60°/31° C. using a BÜCHI Mini Spray Dryer B-290 as described below.

Scanning electron microscopic results: Under electronic microscope, spray dried conidia at an inlet temperature of 60° C. using a BÜCHI Mini Spray Dryer B-290 were raisin shaped and had smooth surfaces (FIG. 4). 8% sucrose solution gave a heavy microencapsulation (FIG. 6), and formed a thick coating on the conidia when compared with spray dried conidia without sugar microencapsulation (FIG. 4) or conidia microencapsulated with 2% sucrose solution (FIG. 5). 2% sucrose solution resulted in well microencapsulated conidia without a thick coating. The particle sizes of microencapsulated conidia were from 10-20 μm.

Discussion: We have shown the surprising success of microencapsulating hydrophilic conidia with trace amount of sugar through spray drying at elevated temperature. Results from this study indicated that microencapsulation with sucrose, molasses, and glycerol protected aerial conidia of *T. harzianum* during rapid drying. Sugar microencapsulation through spray drying at high temperatures forms glass coverage on the conidia (FIG. 5-6) that, without being bound by theory, may have protected the conidia during the rapid dehydration. Sucrose microencapsulation (0.5% to 8% solutions) resulted in significant improvement (P<0.05) in survival percentages after spray drying; however, this improvement was not sucrose concentration dependent, although conidia microencapsulated by 2% sucrose solution had higher survival rate (FIG. 1).

Our study used simple sugars as protection agents for microencapsulation during spray drying. Sugar solutions evaporated rapidly during spray drying and formed a vapor surrounding that keeps conidia at a relatively low temperature in the heat exchange phase. As long as the evaporation exits, the temperature of the microencapsulated particles remained lower than the outlet temperature. Trace amounts of sugar on the conidia eventually form a glass that protected the viability of the conidia.

Applying spray drying techniques in microencapsulation of microbes, especially conidia of hydrophilic filamentous fungi, has many advantages. By adjusting feeding and inlet temperature settings, outlet temperature can be controlled and therefore the heat effects on conidia created by higher inlet temperature can be minimized. Moreover, unlike fluid bed drying or lyphilization, the time that conidia were under high temperature was extremely short. The heat exchange between hot air and conidia particles during drying is evaporation. Evaporation develops vapor surroundings keeping conidia particles at a relatively low temperature. The average particle size of a microencapsulated conidial ball was quite small, usually around 10 to 20 μm, and larger size particles can also be obtained by adjusting the atomizer and pump feeding speed. Only trace amounts of sugar were loaded on the conidia to form spherical particles that were flowable. Flowable particles were easily processed and formulated. Microencapsulated conidia of *T. harzianum* can be mixed with not only other biological control agents, but also microbes that improve plant nutrient uptake and yields, such as *Bradyrhizobium* and *Rhizobium*.

All of the references cited herein, including U.S. patents, are incorporated by reference in their entirety. Also incorporated by reference in their entirety are the following references: U.S. Pat. No. 5,288,634; U.S. Pat. No. 5,989,898; U.S. Pat. No. 6,455,036; PCT/US2006/034744 (2006); Boza, Y., et al., Process Biochemistry, 39: 1275-1284 (2004); Faria, M., et al., Biological Control, 51: 346-354 (2009); Jin, X., et al., Biological Control, 46: 226-233 (2008); Jin, X., et al., Biocontrol Science and Technology, 19: 341-347 (2009); Lyn, M. E., et al., Food Additives and Contaminants, 26: 381-387 (2009).

Thus, in view of the above, the present invention concerns (in part) the following:

A method for encapsulation of microparticles, comprising (or consisting essentially of or consisting of) suspending microparticles in an aqueous solution containing at least one sugar to form an aqueous suspension wherein the concentration of said sugar is about 0.1% to about 10.0% w/v, and spray drying said aqueous suspension with a spray dryer, wherein the inlet temperature of said spray dryer is about 40° C. to about 140° C. and the outlet temperature of said spray dryer is about 20° C. to about 80° C. The method optionally does not involve the use of water absorbent materials such as those described in U.S. Pat. No. 6,455,036 (e.g., starch graft copolymers). The method optionally does not involve the use of sucrose. The method optionally does not involve the use of growth media containing sucrose. The above method wherein said microparticles are hydrophilic.

The above method, wherein said microparticles are a viable cellular biomaterial. The above method, wherein said cellular biomaterial comprises fungal propagules, bacterial cells, protozoa, nematodes, viruses, or mixtures thereof. The above method, wherein said fungal propagules are conidia, spores, hyphal cells, or mixtures thereof. The above method, wherein said fungal propagules are conidia.

The above method, wherein said microparticle are *Bacillus* species, *Entomophaga* species, *Paecilomyces* species, *Metarhizium* species, *Beauveria* species, *Penicillium* species, *Trichoderma* species, *Steinernema* species, *Heterorhabditis* species or mixtures thereof.

The above method, wherein said microparticle are *Bacillus thuringiensis*, *Entomophaga maimaiga*, *Paecilomyce fumosoroseus*, *Metarhizium anisopliae*, *Beauveria bassiana*, *Trichoderma harzianum*, or mixtures thereof.

The above method, wherein said sugar is selected from the group consisting of monosaccharides, disaccharides, polysaccharides, natural gums, molasses, glycerol, honey, corn-syrup, maple syrup, and mixtures thereof.

The above method, wherein said sugar is selected from the group consisting of glucose, fructose, galactose, xylose, ribose, sucrose, lactose, maltose, trehalose, cellobiose, starch, starch derivatives, cellulose, cellulose derivatives, natural gums, molasses, glycerol, honey, corn-syrup, maple syrup, and mixtures thereof.

The above method, wherein said inlet temperature of said spray dryer is about 50° C. to about 80° C. and said outlet temperature of said spray dryer is about 25° C. to about 45° C.

The above method, wherein said inlet temperature of said spray dryer is about 60° C. and said outlet temperature of said spray dryer is about 30° C.

The above method, wherein said microparticles have a size of from about 8 to about 30 μm.

The above method, wherein the amount of said sugar loaded on said encapsulated microparticle is about 2 to about 10 mg per one gram of said encapsulated microparticles.

An encapsulated microparticle produced by the above method.

The above encapsulated microparticle, wherein said microparticle is a viable cellular biomaterial. The above encapsulated microparticle, wherein said biomaterial comprises a fungal propagule selected from the group consisting of conidia, spores and hyphal cells.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for encapsulation of microparticles, comprising suspending microparticles in an aqueous solution containing at least one sugar to form an aqueous suspension wherein the concentration of said sugar is about 0.1% to about 10.0% w/v, and spray drying said aqueous suspension with a spray dryer, wherein the inlet temperature of said spray dryer is about 40° C. to about 140° C. and the outlet temperature of said spray dryer is about 20° C. to about 80° C.; wherein said microparticles are fungal conidia, fungal spores, fungal hyphal cells, or mixtures thereof; wherein the amount of said sugar loaded on said encapsulated microparticle is about 2 to about 10 mg per one gram of said encapsulated microparticles.

2. The method according to claim 1, wherein said microparticles are fungal conidia.

3. The method according to claim 1, wherein said microparticles are *Bacillus* species, *Entomophaga* species, *Paecilomyces* species, *Metarhizium* species, *Beauveria* species, *Penicillium* species, *Trichoderma* species, *Steinernema* species, *Heterorhabditis* species or mixtures thereof.

4. The method according to claim 1, wherein said microparticles are *Bacillus thuringiensis, Entomophaga maimalga, Paecilomyce fumosoroseus, Metarhizium anisopliae, Beauveria bassiana, Trichoderma harzianum*, or mixtures thereof.

5. The method according to claim 1, wherein said sugar is selected from the group consisting of monosaccharides, disaccharides, polysaccharides, natural gums, molasses, glycerol, honey, corn-syrup, maple syrup, and mixtures thereof.

6. The method according to claim 1, wherein said sugar is selected from the group consisting of glucose, fructose, galactose, xylose, ribose, sucrose, lactose, maltose, trehalose, cellobiose, starch, cellulose, natural gums, molasses, glycerol, honey, corn-syrup, maple syrup, and mixtures thereof.

7. The method according to claim 1, wherein said inlet temperature of said spray dryer is about 50° C. to about 80° C. and said outlet temperature of said spray dryer is about 25° C. to about 45° C.

8. The method according to claim 1, wherein said inlet temperature of said spray dryer is about 60° C. and said outlet temperature of said spray dryer is about 30° C.

9. The method according to claim 1, wherein said microparticles have a size of from about 8 to about 30 μm.

* * * * *